(12) United States Patent
Momany et al.

(10) Patent No.: US 12,303,177 B2
(45) Date of Patent: May 20, 2025

(54) PACKAGE FOR MEDICAL DEVICES (71) Applicant: GUARDIAN MEDICAL USA, LLC, Swanton, OH (US)

(72) Inventors: Tracy Momany, Sylvania, OH (US); Roebrt Groll, Oregon, OH (US); Daniel Witham, Sylvania, OH (US); Shari Morse, Temperance, MI (US)

(73) Assignee: GUARDIAN MEDICAL USA, LLC, Swanton, OH (US)

( * ) Notice: Subject to any disclaimer, the term of this patent is extended or adjusted under 35 U.S.C. 154(b) by 115 days.

(21) Appl. No.: 17/758,672

(22) PCT Filed: Jan. 14, 2021

(86) PCT No.: PCT/US2021/013497
§ 371 (c)(1),
(2) Date: Jul. 12, 2022

(87) PCT Pub. No.: WO2021/146469
PCT Pub. Date: Jul. 22, 2021

(65) Prior Publication Data
US 2023/0052702 A1 Feb. 16, 2023

Related U.S. Application Data (60) Provisional application No. 62/960,767, filed on Jan. 14, 2020.

(51) Int. Cl.
*A61B 17/86* (2006.01)
*A61B 50/30* (2016.01)
*A61B 50/00* (2016.01)

(52) U.S. Cl.
CPC ............ *A61B 17/865* (2013.01); *A61B 50/30* (2016.02); *A61B 2050/0054* (2016.02)

(58) Field of Classification Search
CPC .................. A61B 17/365; A61B 50/30; A61B 2050/0054; A61B 17/865
USPC .................................................. 306/63.5, 339
See application file for complete search history.

(56) References Cited

U.S. PATENT DOCUMENTS

| 5,622,500 | A | 4/1997 | Niznick | |
| 7,694,812 | B2 * | 4/2010 | Bammerlin | A61C 8/0087 |
| | | | | 206/63.5 |
| 10,398,523 | B2 | 9/2019 | Roesler et al. | |
| 2006/0243616 | A1 * | 11/2006 | Caron | A61B 50/30 |
| | | | | 206/349 |
| 2010/0236947 | A1 * | 9/2010 | Liao | A61C 8/0087 |
| | | | | 206/63.5 |
| 2017/0095308 | A1 | 4/2017 | Roesler et al. | |
| 2017/0166377 | A1 | 6/2017 | Kaplan et al. | |

(Continued)

FOREIGN PATENT DOCUMENTS

| JP | 3188325 U | 1/2014 |
| WO | 2019030451 A2 | 2/2019 |
| WO | 2019161186 A1 | 8/2019 |

*Primary Examiner* — Jacob K Ackun
(74) *Attorney, Agent, or Firm* — Michael E. Dockins; Shumaker Loop & Kendrick LLP (57) ABSTRACT A package assembly for carrying medical devices is disclosed. The package assembly includes an outer cartridge and an inner cartridge. The inner cartridge receives the outer cartridge of the package assembly. The inner cartridge extends beyond the outer cartridge. A medical device is disposed in the inner cartridge to engage the inner cartridge.

6 Claims, 6 Drawing Sheets (56) References Cited

U.S. PATENT DOCUMENTS

2019/0336188 A1 11/2019 Agarwal et al.
2020/0197120 A1* 6/2020 Folger .................... A61B 50/30
2021/0077242 A1* 3/2021 Agarwal ................ A61B 50/00

* cited by examiner

PACKAGE FOR MEDICAL DEVICES

CROSS REFERENCE TO RELATED APPLICATIONS

This application is a National Stage application of International Application No. PCT/US21/13497, filed on Jan. 14, 2021, which claims the benefit of U.S. Provisional Application No. 62/960,767, filed on Jan. 14, 2020. The entire disclosure of each of the above-identified patent applications is hereby incorporated herein by reference.

FIELD

The present invention relates generally to packages for medical devices, and more particularly to receptacles configured to secure various medical devices of a similar or common geometry within a single receptacle for antiseptic transportation.

BACKGROUND OF THE INVENTION

As is commonly known, medical devices, such as those used for implanting or using on a patient must be sterile, undamaged, or otherwise compromised before implanting or using on the patient. Particularly, the medical devices are transporting from a manufacturer, distributor, medical-related facility, and/or area that may or may not be sterile to a facility or space that is required to be sterile. Therefore, packaging is used to transport the medical devices into a sterile atmosphere.

However, certain packaging for medical devices can be unstable or unsupportive of the device in transport, wherein the medical device moves around undesireably in the package to cause damage. This is often due to the fact medical devices are designed to be customizable to a patient and the needs of the patient. As such, one type of packaging may not be suitable or accommodating to each and every medical device to deliver the medical device undamaged and sterile. In many instances, one type of packaging is used to accommodate many devices even though they have differing sizes, shapes, and geometry which results in some of the medical devices be unsecure in the package because the devices may move around therein. Alternatively, in other instances, a package may be used for each and every varying type of medical device which can be very costly.

Additionally, an interest in ergonomic, sterile, and efficient ease of removal of the devices is becoming increasing more desired. As such a hermetically sealed type package that also allows for the contents therein to be removed and safety passed to sterile zones is desired. Furthermore, a safe and organized storage of the medical devices within the packaging is also desired.

Therefore it is desirable to have a rigid sterile medical device package that is capable of securing related or similar medical devices having common geometry within the same holder that minimizes cost in producing custom packing.

SUMMARY OF THE INVENTION

In concordance and agreement with the present invention, a rigid sterile medical device package that is capable of securing related or similar medical devices having common geometry within the same holder that minimizes cost in producing custom packing has surprisingly been discovered.

In a first embodiment of the present disclosure, a package assembly for carrying medical devices is disclosed. The package assembly includes an outer cartridge and an inner cartridge. The inner cartridge receives the outer cartridge of the package assembly. The inner cartridge extends beyond the outer cartridge. A medical device is disposed in the inner cartridge to engage the inner cartridge.

In another embodiment of the disclosure, a package assembly for carrying medical devices is disclosed. The assembly includes an outer cartridge and an inner cartridge receiving the outer cartridge. The inner cartridge extends beyond the outer cartridge. A medical device is disposed in the inner cartridge, wherein the medical device expands beyond the inner cartridge.

In yet another embodiment of the disclosure, a package assembly for carrying medical devices is disclosed. The assembly includes an outer cartridge including a cap and a main body and an inner cartridge receiving the outer cartridge. The inner cartridge extends beyond the outer cartridge. The inner cartridge includes a cap and main body and a medical device is disposed in the inner cartridge, wherein the medical device expands beyond the inner cartridge.

BRIEF DESCRIPTION OF THE DRAWINGS

The above-mentioned, and other features and objects of the invention, and the manner of attaining them will become more apparent and the invention itself will be better understood by reference to the following description of an embodiment of the invention taken in conjunction with the accompanying drawings, wherein.

DESCRIPTION OF THE PREFERRED EMBODIMENT

The following detailed description and appended drawings describe and illustrate various exemplary embodiments of the invention. The description and drawings serve to enable one skilled in the art to make, and use the invention, and are not intended to limit the scope of the invention in any manner. With respect to the methods disclosed, the steps presented are exemplary in nature, and thus, the order of the steps is not necessary or critical.

A" and "an" as used herein indicate "at least one" of the item is present; a plurality of such items may be present, when possible. Spatially relative terms, such as "front," "back," "inner," "outer," "bottom," "top," "horizontal," "vertical," "upper," "lower," "side," "above," "below," "beneath," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures.

As used herein, substantially is defined as "to a considerable degree" or "proximate" or as otherwise understood by one ordinarily skilled in the art. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters. Where any conflict or ambiguity may exist between a document incorporated by reference and this detailed description, the present detailed description controls. Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

The present invention relates to packages for transporting medical devices to a sterile work zone such as an area of an operating room. Examples of medical devices are given throughout the disclosures. For example, medical devices can refer to a screws, implants, and the like all of varying dimensions or geometries. However, it is understood the packages can be used to transport any other device for any other application. Additionally, the application uses the term "family" which is meant to refer to devices employed together on a patient or used simultaneously or within the same operating time or operating room. The term "family" can also refer to varying medical devices of different sizes and shapes that have at least one common geometry the package can accommodate for transporting without customizing a new package.

Figure 1:
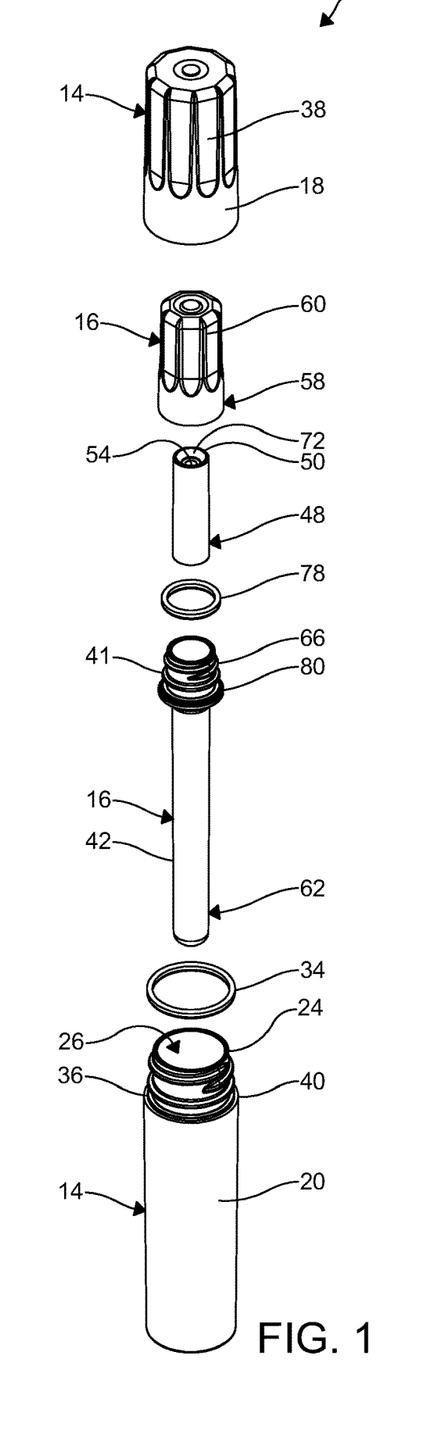
FIG. 1 is an exploded perspective view of a package assembly according to the invention.
Figure 2:
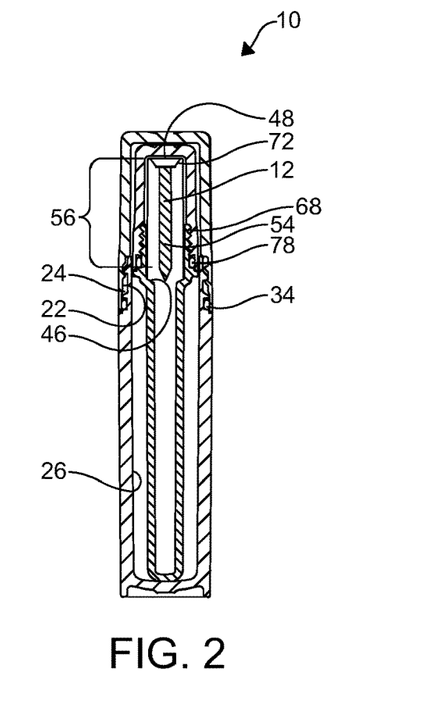
FIG. 2 is a cross-sectional front elevation view of the package assembly according to FIG. 1, wherein a medical device is shown therein.

FIGS. 1-2 illustrate a package assembly 10 according to an embodiment of the instant disclosure. The package assembly 10 is configured for transporting a medical device 12, described herein below. The package assembly 10 includes an outer cartridge 14, an inner cartridge 16, and the device 12.

The outer cartridge 14 includes a cap 18 and a main housing 20 threading engaging each other. The cap 18 of the outer cartridge 14 includes threads 22 disposed on an internal surface thereof. The main housing 20 of the outer cartridge 14 includes threads 24 disposed on an outer surface thereof. The threads 24 of the main housing 20 engage and receive the threads 24 of the cap 18. The cap 18 and the main housing 20 cooperate with each other to define an inner chamber 26 of the outer cartridge 14. In the embodiment illustrated, the outer cartridge 14 is substantially cylindrical in shape. However, it is understood the outer cartridge 14 can have any shape as desired such as cubical, spherical, having a polygonal cross-sectional shape, having a ovular cross-sectional shape, pyramidal, or any shape or combination of shapes as desired. An outer cartridge seal 34 configured as an annular resilient seal such as an o-ring, for example, is disposed between a shoulder 36 and an end of the cap 18. It is understood, the seal 34 can be configured as a metal seal or plastic seal or any other seal as desired.

The cap 18 of the outer cartridge 14 includes a plurality of grip features 38. As shown, the grip features 38 are indentations formed in an outer surface of the cap 18. However, the grip features 38 can be ridges, a finger grip, or any other grip-type feature as desired.

The inner cartridge 16 includes a cap 58 with threads 68 formed on an inner surface thereof, and main body 62 and threads 66 formed on an outer surface thereof. The threads 68 of the cap 58 engage the threads 66 of the main body 62.

The main body 62 includes a threaded portion 41 that contains the threads 66 of the internal cartridge 16 of the main body 62 and a receiving portion 42 for receiving the medical device 12. The receiving portion 42 is a tube and has an inner diameter less than an inner diameter of the threaded portion 41. The receiving portion 42 is substantially cylindrical. However, other shapes can be employed as desired. The difference in the diameters facilitates a stable disposal of the medical device 12. An inner cartridge seal 78 configured as an annular resilient seal such as an o-ring, for example, is disposed between a shoulder 80 and an end of the cap 58. It is understood, the seal 78 can be configured as a metal seal or plastic seal or any other seal as desired.

An inner surface 44 of the threaded portion 41 of the inner cartridge 16 includes a shoulder 46 for stopping a stabilizer 48 being received through an opening of the threaded portion 41 and extending through the receiving portion 42. The stabilizer 48 is annular and has a first end 50 for receiving the medical device 12 and a second end 52 for conveying the medical device 12 threrethrough into the receiving portion 42 of the inner cartridge 16. The stabilizer 48 includes an inner aperture 54 extending therethrough with respect to a length thereof. An inner diameter of the stabilizer 48 at the first end 50 is greater than an inner diameter of the 48 stabilizer in an intermediate section 56 thereof. A cross-sectional shape of the stabilizer 48 at the first end has a frustoconical portion 72 configured to receive the medical device 12 such as a head 74 of a screw, wherein the remainder of the inner aperture 54 of the stabilizer 48 is for receiving a stem 76 of elongated part of the medical device 12. A diameter of the frustoconical portion 72 increases constantly from adjacent the intermediate section 56 to the first end 52 of the stabilizer 48. As a result, the head 74 of the medical device 12 is stabilized and supported.

As shown in FIG. 2, the main body 62 of the inner cartridge 16 extends beyond the main housing 20 of the outer cartridge 14. As shown the threads 66 of the inner cartridge 16 extend beyond the threads 24 of the outer cartridge 14 with respect to a length direction of the outer cartridge 14 in a direction towards the cap 18 of the outer cartridge 14. The threads 66 of the internal cartridge 16 extending beyond the threads 24 of the outer cartridge 14 is advantageous to grip and receive the inner cartridge 16 in a sterile setting. The stabilizer 48 extends beyond the threaded portion 41 of the inner cartridge 16 towards a cap 58 of the inner cartridge 16.

The cap 58 of the inner cartridge 16 includes a plurality of grip features 60. As shown, the grip features 60 are indentations formed in an outer surface of the cap 58. However, the grip features 60 can be ridges, a finger grip, or any other grip-type feature as desired. The threaded portions 68 of the cap 58 engage the threads 66 of the main body 62.

In application, the inner cartridge 16 is removed from the outer cartridge 14. The inner cartridge 16 remains sterile. The cap 58 of the inner cartridge 16 is removed in a sterile environment. Because the stabilizer 48 extends outwardly from the inner cartridge 16, the stabilizer can be easily removed with the medical device 12.

Figure 3:
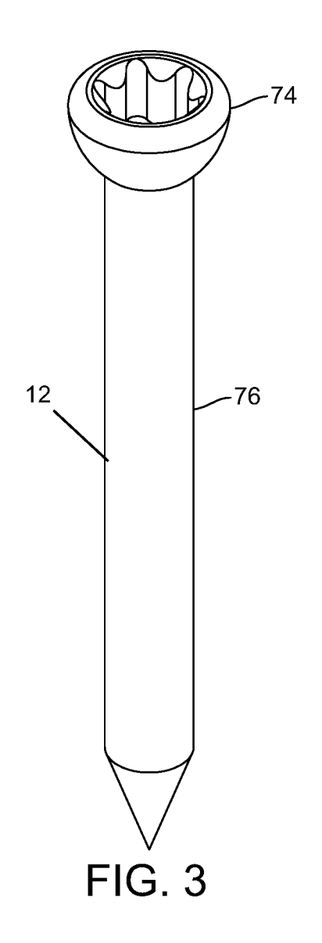
FIGS. 3-5 illustrate top perspective views of various embodiments of medical devices that can be inserted into the package assembly of FIGS. 1-2.
Figure 4:
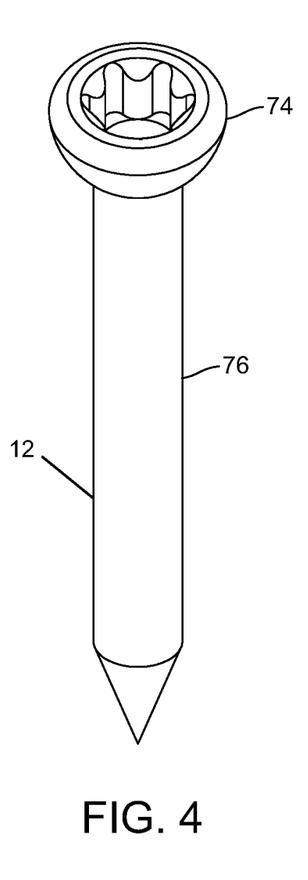
Figure 5:
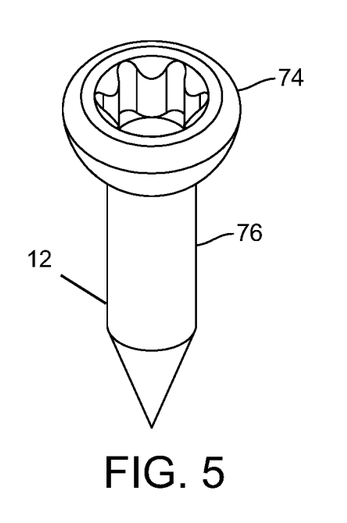

FIGS. 3-5 illustrate various types of the medical devices 12. In the embodiments, each of the medical devices 12 are configured as screws with the head 74 and the stem 76. However, the medical devices 12 can be any medical devices configured with a head and stem as desired that can be packaged and transported in the package assembly 10. Each of the medical devices 12 shown have a common geometry being the head 74 and the stem 76. Therefore, even though a length among the medical devices 12 and a thread design are different, each of the medical devices shown can be interchangeably packaged in the package assembly 10 of FIGS. 1-2. Advantageously, a separate package geometry does not have to be manufactured for each different medical device.

Figure 6:
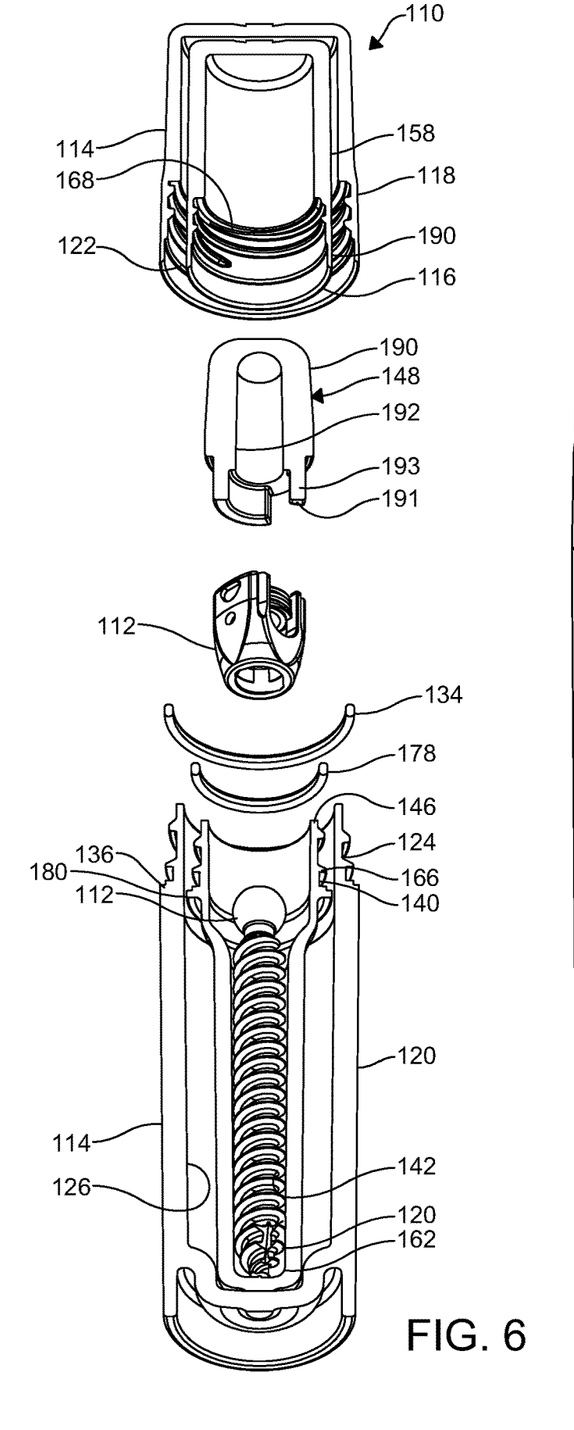
FIG. 6 is an exploded cross-sectional perspective view of a package assembly according to another embodiment of the disclosure.
Figure 7:
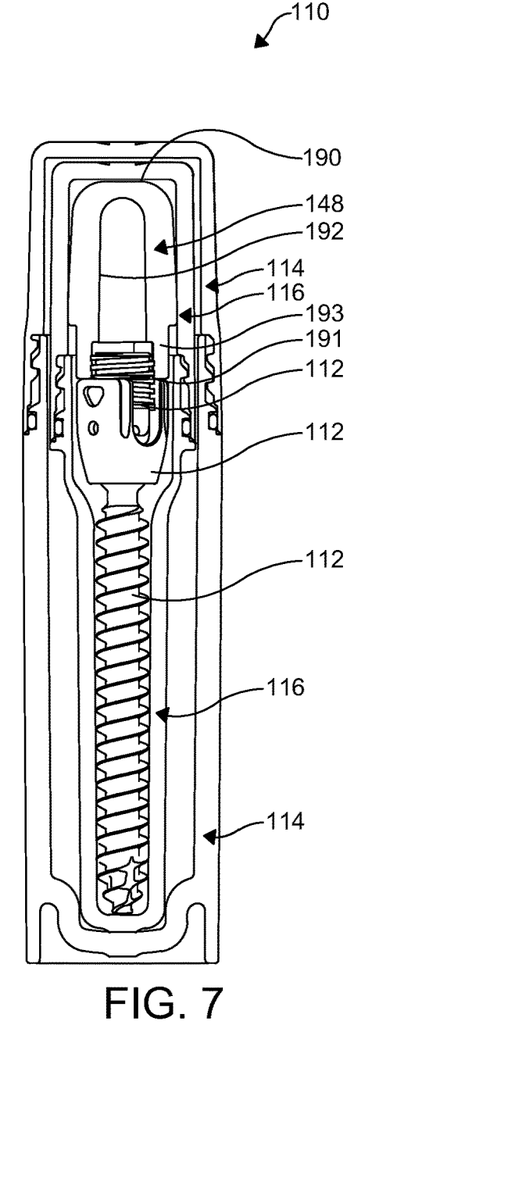
FIG. 7 is an assembled cross-sectional front elevation view of the package assembly of FIG. 6.

FIGS. 6-7 illustrate a package assembly 110 according to another embodiment of the instant disclosure. The package assembly 110 of FIGS. 6-7 include features similar to the features of the package assembly 10 of FIGS. 1-2. Features of the package assembly 110 similar to the features of the package assembly 10 of FIGS. 1-2 are referenced with the same reference numerals but with a leading one "1" for convenience. The package assembly 110 is similar to the package assembly 10 of FIGS. 1-2, except the stabilizer 148 is different. The package assembly 110 is configured for medical devices with a tulip, screw, and set screw.

The stabilizer 148 of FIGS. 6-7 is configured as a cap insert. The stabilizer 148 is cylindrical in shape and includes a closed end 190 and an open end 191. An aperture 192 extends through the stabilizer 148 inwardly from the open end 191 of the stabilizer 148. A diameter of the aperture 192 adjacent the open end 191 is larger than a diameter of an inner portion of the stabilizer. The aperture 192 adjacent the open end 191 is configured to receive the medical device 112 such as a set screw. The stabilizer 148 is configured to have an outer contour to substantially fill an inner contour of the cap 158 of the inner cartridge 116. The open end 191 has a pair of notches 193 formed therein to facilitate removal of the medical device 112 disposed therein.

To assemble, a first portion of the medical device 112 is received in the inner cartridge 116. As shown, the inner cartridge 116 has an inner contour for receiving the medical device 112. The stabilizer 148 receives a second portion of the medical device 112 such as a set screw in the open end 191 thereof. The stabilizer 148 is then positioned to engage the first portion of the medical device 112. The cap 158 of the inner cartridge 116 is then threaded onto the main body 162 to secure the stabilizer 148 and the medical device 112 therein. The inner cartridge 116 is then secured within the outer cartridge 114. Once assembled, the package assembly 110 can then be transported to a desired location and disassembled in a sterile environment.

Figure 8:
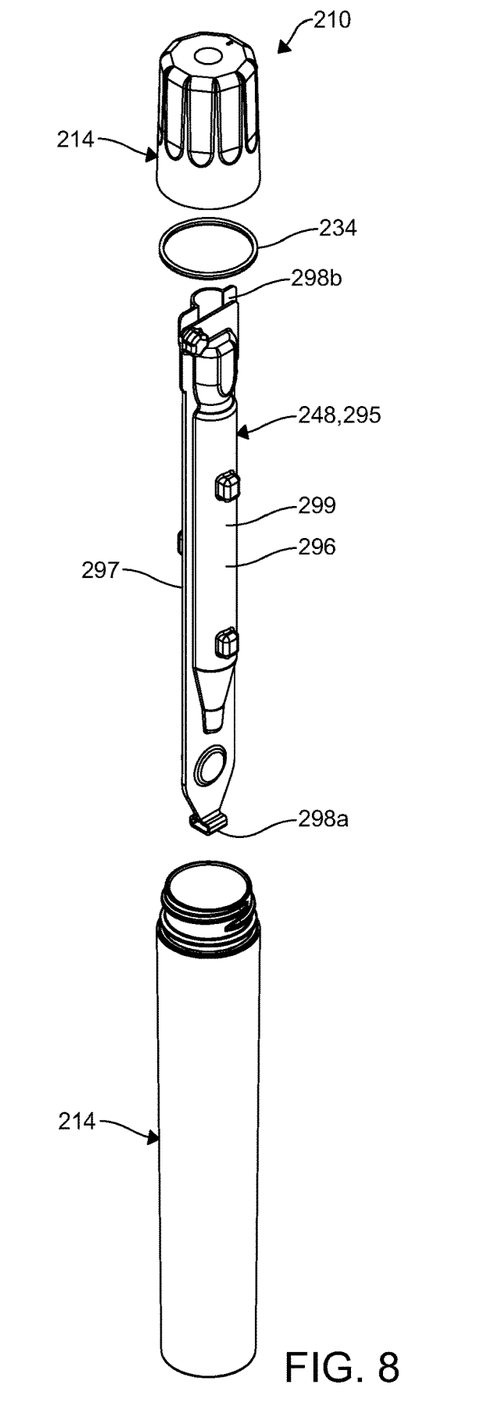
FIG. 8 is an exploded perspective view of a package assembly according to another embodiment of the disclosure.
Figure 9:
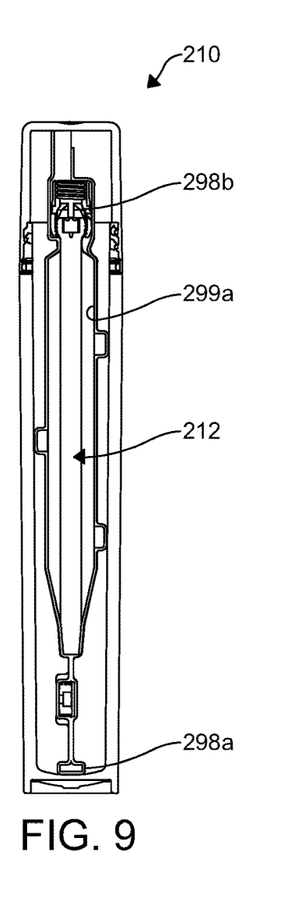
FIG. 9 is a cross-sectional front elevation view of the package assembly of FIG. 8.

FIGS. 8-9 show a package assembly 210 according to another embodiment of the disclosure. The package assembly 210 of FIGS. 8-9 include features similar to the features of the package assembly 10, 110 of FIGS. 1-2 and 6-7. Features of the package assembly 210 similar to the features of the package assembly 10 of FIGS. 1-2 are referenced with the same reference numerals but with a leading two "2" for convenience. The package assembly 210 is similar to the package assembly 10 of FIGS. 1-2, except the stabilizer 248 is different. The package assembly 210 is configured for medical devices with a tulip, screw, and set screw. Additionally, the inner cartridge is not employed, wherein a clam shell receptacle 295 is used.

Figure 10:
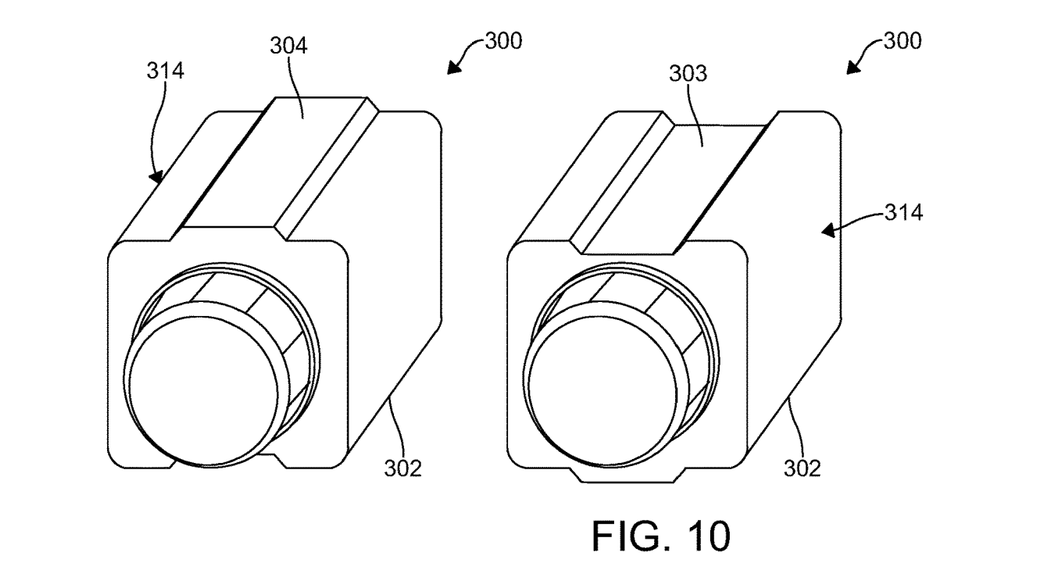
FIG. 10 illustrates a pair of package assemblies according to another embodiment of the disclosure, wherein the pair of package assemblies are shown in a side-by-side position.
Figure 11:
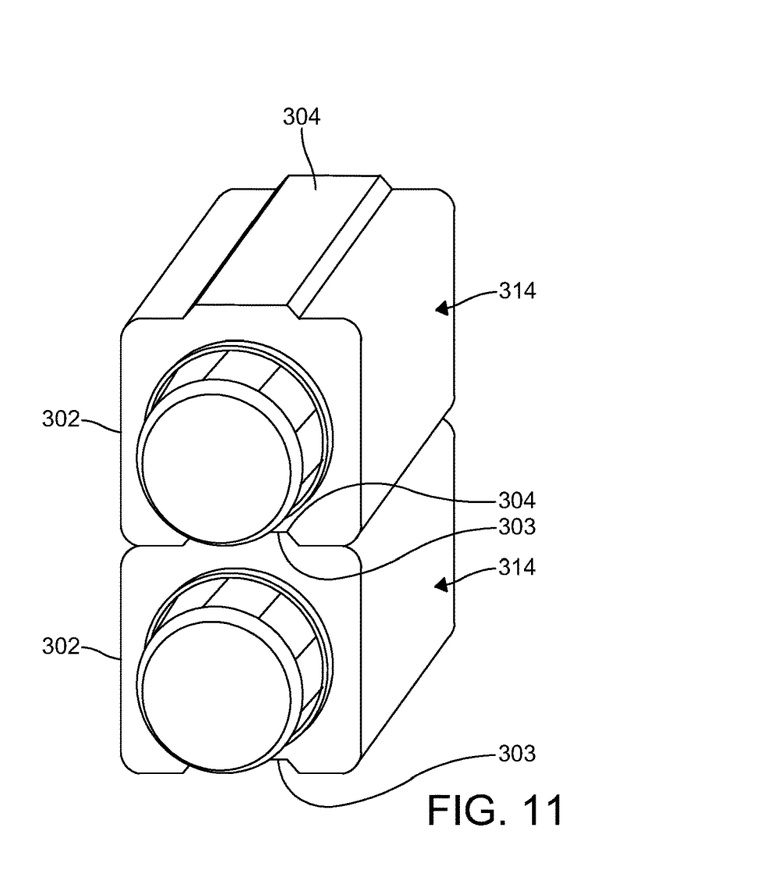
FIG. 11 illustrates the pair of package assemblies of FIG. 10, wherein the pair of package assemblies are shown in a stacked position.

The stabilizer 248 includes the clam shell receptacle 295 configured to receive the medical device 212 shown in FIGS. 10-11. The clam shell receptacle 295 includes a first side 296 and a second side 297 with features configured to receive the medical device 212. The first side 296 and the second side 297 can be substantially mirror images of each other and fold along a pivot portion 298a. However, it is understood the first side 296 and the second side 297 can be different from each other. The first side 296 and the second side 297 each have indentations 299 to form an inner chamber 299a for the medical device 212. The receptacle 295 can receive like ones of the medical devices 212 even if the medical devices 212 have varying lengths and widths. A common geometry of like ones of the medical devices 212 can be received in the receptacle 295. A tab end 298b includes means such as a tab, for example, so the first side 296 and the second side 297 can be separated from each about the pivot portion 198 to remove the medical device 212 therefrom.

Figure 12:
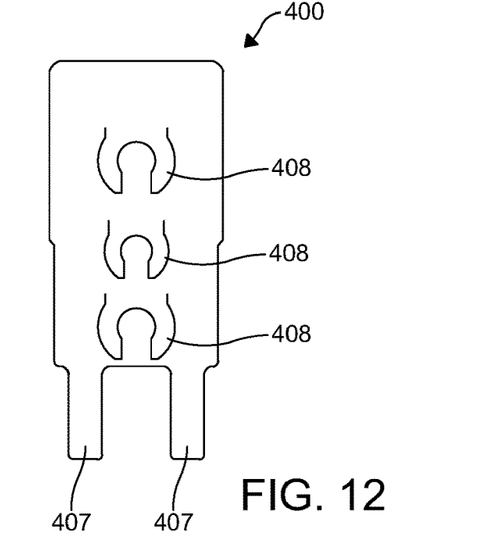
FIG. 12 illustrates a top plan view of a sleeve for a package assembly according to another embodiment of the present disclosure.
Figure 13:
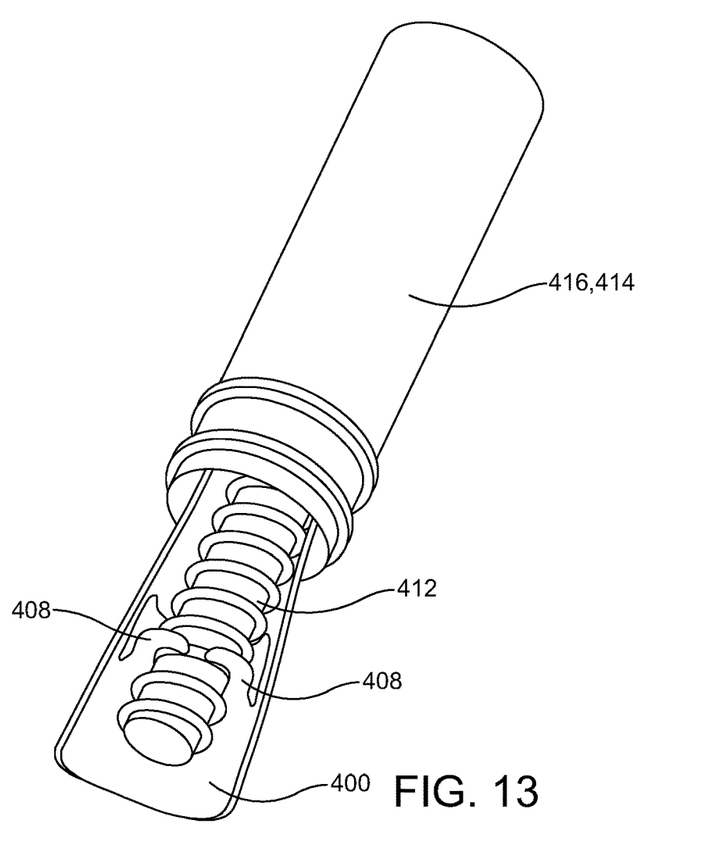
FIG. 13 illustrates a perspective view of the sleeve receiving a medical device and being inserted into a package assembly according to an embodiment of the disclosure.

FIGS. 10-11 show an outer package 300 that can be employed to house a medical device 312. A blow molded housing 302 is used to house the medical device 312. The housing 302 has an indentation 303 for receiving other ones of the outer package 300 for stacking that have protrusions 304 formed thereon FIGS. 12-13 show a card 400 for receiving the medical device 412. The card 400 includes a plurality of poppable u-shaped holders 408 for receiving the medical device 412. As shown, in FIG. 15, the medical device 412 is coupled to the u-shaped holders 408 and the card 400 is curved around the medical device 412 to hold the card 400 and the medical device 412 securely in the package assembly 410. The card 400 may also have extensions 407 to permit the card 400 to protrude from either the inner cartridge 416 and/or the outer cartridge 414. Additionally, the extensions 407 serve as a grip for grabbing the card 400 should the card 400 remain in a cap coupled to the inner cartridge 416 or outer cartridge 414.

From the foregoing description, one ordinarily skilled in the art can easily ascertain the essential characteristics of this invention and, without departing from the spirit and scope thereof, can make various changes and modifications to the invention to adapt it to various usages and conditions.

What is claimed is:

1. A package assembly comprising:
   a medical device having a head and a stem;
   an outer cartridge configured to receive an inner cartridge,
      the outer cartridge including an outer cartridge main body and an outer cartridge cap, the outer cartridge main body and the outer cartridge cap cooperating to define an inner chamber of the outer cartridge, the inner cartridge received in the inner chamber of the outer cartridge, the inner cartridge including an inner cartridge main body and an inner cartridge cap, the inner cartridge main body including an inner surface defining an opening including a receiving portion, the medical device disposed in the inner cartridge; and a stabilizer received in the outer cartridge and configured to be received within the opening of the inner cartridge main body, the stabilizer having an inner aperture extending lengthwise through the stabilizer from a first end of the stabilizer to a second end thereof, and wherein the medical device is received within the inner aperture of the stabilizer with the head of the medical device axially restrained between the stabilizer and an inner surface of the inner cartridge cap at or adjacent the first end of the stabilizer and the stem of the medical device extending from the head of the medical device into the inner aperture or through the inner aperture beyond the second end of the stabilizer and into the receiving portion of the inner cartridge main body.

2. The package assembly of claim 1, wherein the inner aperture includes a first portion disposed towards and extending to the first end of the stabilizer and a second portion disposed towards and extending to the second end of the stabilizer, wherein an inner diameter of the first portion of the inner aperture at the first end of the stabilizer is greater than an inner diameter of the second portion of the inner aperture, and wherein the first portion of the inner aperture is tapered such that the inner diameter of the first portion of the inner aperture decreases from the first end of the stabilizer towards the second portion of the inner aperture, and wherein the head of the medical device is disposed within the first portion of the inner aperture and the stem of the medical device extending from the head of the medical device into the second portion of the inner aperture or through the second portion of the inner aperture and configured to be disposed into the receiving portion of the inner cartridge main body.

3. The package assembly of claim 1, wherein the medical device is a screw.

4. The package assembly of claim 1, wherein the stabilizer is cylindrical.

5. The package assembly of claim 1, wherein the head of the medical device is configured to be disposed outside of the inner cartridge main body.

6. A package assembly for carrying medical devices comprising:

an outer cartridge including an outer cartridge main body and an outer cartridge cap, the outer cartridge configured to receive an inner cartridge, the inner cartridge received in the outer cartridge, the inner cartridge including an inner cartridge main body and an inner cartridge cap; and a stabilizer configured to be disposed in the inner cartridge, wherein a portion of the stabilizer extends outside of the inner cartridge main body and into the inner cartridge main body, the stabilizer configured to receive varying medical devices having at least one common geometry.

\* \* \* \* \*

UNITED STATES PATENT AND TRADEMARK OFFICE
CERTIFICATE OF CORRECTION

Page 1 of 1

PATENT NO. : 12,303,177 B2
APPLICATION NO. : 17/758672
DATED : May 20, 2025
INVENTOR(S) : Tracy Momany et al.

It is certified that error appears in the above-identified patent and that said Letters Patent is hereby corrected as shown below:

On the Title Page

Item (72) The second inventor currently reads: Roebrt Groll
The name should read: Robert Groll Signed and Sealed this
Eighth Day of July, 2025

Coke Morgan Stewart
*Acting Director of the United States Patent and Trademark Office*